(12) United States Patent
Taylor et al.

(10) Patent No.: US 6,605,475 B1
(45) Date of Patent: Aug. 12, 2003

(54) APPARATUS AND METHOD FOR SAMPLE DELIVERY

(75) Inventors: Todd A. Taylor, Framingham, MA (US); William W. Carson, Hopkinton, MA (US); Xian-Wei Yao, Edison, NJ (US)

(73) Assignee: Perspective Biosystems, Inc., Framingham, MA (US)

( * ) Notice: Subject to any disclaimer, the term of this patent is extended or adjusted under 35 U.S.C. 154(b) by 0 days.

(21) Appl. No.: 09/293,314

(22) Filed: Apr. 16, 1999

(51) Int. Cl.⁷ .......................... G01N 1/10; G01N 15/06; G01N 21/00; G01N 31/22; B01L 3/02; B01L 3/00; F27B 15/14; F27B 15/16; F01N 3/10; F24H 1/10

(52) U.S. Cl. ................ 436/180; 204/274; 422/99; 422/100; 422/58; 422/68.1; 422/146; 422/173; 219/521; 392/482; 392/484; 392/480

(58) Field of Search .................. 422/58, 59, 68.1, 422/157, 146, 147, 164, 172, 99, 173; 436/180; 204/265, 271, 274; 374/20, 39, 43, 54; 219/521; 392/465–466, 480–482, 484; 165/110

(56) References Cited

U.S. PATENT DOCUMENTS

| | | | |
|---|---|---|---|
| 1,584,267 A | * | 5/1926 | Young |
| 2,653,214 A | * | 9/1953 | Shaw |
| 2,770,707 A | * | 11/1956 | Jordan |
| 2,932,718 A | * | 4/1960 | Marsters |
| 4,315,754 A | | 2/1982 | Ruzicka et al. |
| 4,426,451 A | | 1/1984 | Columbus |
| 4,683,195 A | | 7/1987 | Mullis et al. |
| 4,845,025 A | * | 7/1989 | Lary et al. ............ 435/2 |
| 4,906,344 A | | 3/1990 | Hjerten |
| 4,979,365 A | | 12/1990 | Baker ................ 60/528 |
| 5,000,919 A | * | 3/1991 | Heckmann .......... 422/58 |
| 5,089,232 A | * | 2/1992 | May ................ 422/83 |
| 5,240,576 A | | 8/1993 | Lauer et al. .......... 204/180.1 |
| 5,273,907 A | | 12/1993 | Malmquist |
| 5,287,758 A | | 2/1994 | Geiss et al. |
| 5,302,264 A | | 4/1994 | Welch et al. ......... 204/180.1 |
| 5,304,487 A | | 4/1994 | Wilding et al. |
| 5,410,130 A | * | 4/1995 | Braunstein |
| 5,500,071 A | | 3/1996 | Kaltenbach et al. |
| 5,645,702 A | | 7/1997 | Witt et al. |
| 5,646,048 A | | 7/1997 | Templin et al. |
| 5,650,846 A | | 7/1997 | Yin et al. |
| 5,700,695 A | * | 12/1997 | Yassinzadeh et al. ...... 436/180 |
| 5,720,923 A | | 2/1998 | Haff et al. |
| 5,770,029 A | * | 6/1998 | Nelson et al. ......... 204/604 |
| 5,779,868 A | | 7/1998 | Parce et al. .......... 204/604 |
| 5,866,345 A | * | 2/1999 | Wilding et al. ........ 435/7.21 |

(List continued on next page.)

FOREIGN PATENT DOCUMENTS

| | | |
|---|---|---|
| CA | 2058648 | 7/1992 |
| EP | 0 608 120 | 7/1994 |
| WO | WO 93/22053 | 11/1993 |
| WO | WO 93/22054 | 11/1993 |
| WO | WO 96/04547 | 2/1996 |
| WO | WO 97/22825 | 6/1997 |

Primary Examiner—Jill Warden
Assistant Examiner—Brian R Gordon

(57) ABSTRACT

Apparatus and methods have been developed to deliver automatically a sample to a reaction vessel, an analytical device or any location where sample introduction or deposition is desired. A sample delivery system of the invention generally includes a housing defining a channel, e.g., a capillary, and a volume controller, which is a temperature control device, in thermal communication with the channel. The channel preferably is closed at one end, and contains an opening for introduction of a sample. The closed end of the channel is associated thermally with the temperature control device. The temperature control device heats and cools a thermally expandable fluid in the channel which controls movement of a sample into, within and out of the channel.

23 Claims, 7 Drawing Sheets

U.S. PATENT DOCUMENTS

| | | | |
|---|---|---|---|
| 5,958,344 A * | 9/1999 | Levine et al. | 422/103 |
| 5,976,336 A | 11/1999 | Dubrow et al. | 204/453 |
| 6,048,495 A * | 4/2000 | Marcoll | 422/60 |
| 6,086,740 A * | 7/2000 | Kennedy | 204/601 |
| 6,150,180 A * | 11/2000 | Parce et al. | 436/514 |
| 6,165,271 A * | 12/2000 | Zhao et al. | 118/715 |
| 6,235,471 B1 * | 5/2001 | Knapp et al. | 435/6 |
| 6,306,590 B1 * | 10/2001 | Mehta et al. | 435/6 |
| 6,375,817 B1 | 4/2002 | Taylor et al. | 204/453 |
| 6,375,901 B1 * | 4/2002 | Robotti et al. | 422/103 |
| 6,428,987 B2 * | 8/2002 | Franzen | 435/91.2 |
| 6,444,461 B1 * | 9/2002 | Knapp et al. | 435/283.1 |
| 2002/0009392 A1 * | 1/2002 | Wolk et al. | 422/63 |
| 2002/0015667 A1 * | 2/2002 | Chow | 422/100 |
| 2002/0054835 A1 * | 5/2002 | Robotti et al. | 422/103 |
| 2002/0086439 A1 * | 7/2002 | Nagle et al. | 433/180 |

\* cited by examiner

APPARATUS AND METHOD FOR SAMPLE DELIVERY

FIELD OF THE INVENTION

The present invention is directed to apparatus and methods for sample delivery. More specifically, the invention is directed apparatus and methods for automated microscale sample delivery to chemical reagents and/or analytical apparatus.

BACKGROUND OF THE INVENTION

Methods for conducting chemical reactions often require multiple steps in multiple reaction vessels involving extensive handling of reagents. These limitations may result in experimental error, contamination, and a risk of exposure of laboratory workers to hazardous substances.

Analytical techniques typically require a high degree of labor and the use of complex apparatus. Moreover, many laboratory and industrial chemical processes involve the use of relatively large volumes of reagents and multiple laboratory instruments. Typical large scale immunoassays, e.g., require the use of pipettes, reagent vessels, and reaction chambers. See, e.g., Mattiasson et al., *Proc. Int. Symp. on Enzyme-Labeled Immunoassay of Hormones and Drugs*, (Pal, S., Ed., Walter de Gruyter, Berlin (1978), p. 91). Such processes, regardless of the size of the reaction, also may require multiple steps. Accordingly, there is a potential for reduced accuracy due to the introduction of impurities, volumetric inaccuracies, and low reproducibility. These problems especially are acute in microscale diagnostic applications in which biological samples are analyzed, such as, e.g., immunoassays, polynucleotide amplifications, or hybridizations.

Recently, efforts have been made to streamline chemical processes to reduce costs, increase accuracy, and improve reaction yields. For example, capillary electrophoresis techniques have been proposed to increase resolution in immunoassays. Various attempts have been made to enhance other common analytical techniques, such as the polymerase chain reaction (PCR). For example, U.S. Pat. No. 5,273,907 reports a capillary pre-loaded with PCR reagents which is used to deliver a sample to the reagents for DNA amplification. Similarly, International Patent Publication WO 93/22058 describes a microscale device for performing PCR. In this case, PCR reagents from a first chamber are mixed with sample in a second chamber by movement of materials through channels in a microchip.

There is a need in the art for methods and apparatus which decrease the labor, cost, biohazard exposure and complexity associated with microscale sample delivery for chemical reactions and analytical techniques. The present invention addresses these needs.

SUMMARY OF THE INVENTION

Apparatus and methods now have been developed to deliver automatically a sample to a reaction vessel, an analytical device or any location where sample introduction or deposition is desired. Broadly, the invention relates to a thermally-controlled microscale sample delivery system and methods of its use. An embodiment of the invention includes apparatus and methods for delivery of a sample to a channel wherein chemical reactions occur.

A sample delivery system of the invention generally comprises a housing defining a channel, e.g., a capillary, and a temperature control device in thermal communication with the channel. The channel preferably is closed at one end, and contains an opening for introduction of a sample. The closed end typically is associated with the temperature-control device. The temperature control device may be a thermoelectric heater, such as a Peltier element, for heating and cooling a thermally expandable fluid in the channel. The temperature control device also may include a temperature controlled fluid which is in thermal communication the channel.

A sample delivery system of the invention preferably includes an array of independent channels so multiple samples simultaneously may be delivered. The channels often are capillaries which may have non-wettable surfaces. In another embodiment of the invention, the channels are capillaries having immobilized therein at least one chemical reagent. In a preferred embodiment, a reagent is pre-loaded into a capillary by immobilization e.g., by drying the reagent on the walls of the capillary. Reagents also may be immobilized by absorption into a plug of material, such as cotton, which is placed in the capillary. Reagents typically are immobilized on the capillary walls in one or more discrete locations.

Another embodiment of the sample delivery system includes a second temperature control device. The second temperature control device may be positioned for heating and/or cooling the sample and reagents in the capillary. The second temperature control device preferably comprises a first conduit for heating and a second conduit for cooling. The second temperature control device, therefore, is adapted for controlling the temperature in a discrete portion of the capillary, typically towards the open end of the capillary. That is, the second temperature control device should not induce temperature changes of the fluid or gas near the closed end of the capillary. To this end, a sample delivery system also may include an insulator partition within the capillary to assist in maintaining a volume of sample stationary within the capillary.

Accordingly, the local temperature of a reaction between reagents and sample may be controlled by a second temperature control device without moving the sample in the capillary or by moving the second temperature control device along the capillary. A sample delivery system of the invention may contain more than two temperature control devices. However, a single temperature control device may be used to heat and/or cool both the entire capillary and discrete locations. A sample delivery system of the invention may contain more than two temperature control devices.

Methods of the invention provide for the delivery of a sample to predisposed reagents within a channel, to an input port of an analytical device or to another location where the sample or its reaction products are desired. In a preferred embodiment, a temperature control device in association with a capillary heats the gas in the capillary so that the volume occupied by the gas increases, thereby increasing its pressure. This increase in volume and pressure forces gas through the capillary opening. The opening of the capillary then is exposed to a sample, e.g., by submerging the open end in a liquid sample. Upon cooling, the volume of gas remaining in the channel contracts, and the pressure within the capillary decreases. Consequently, an aliquot of sample is drawn into the capillary to fill the volumetric void left by the contracting gas. If sufficiently cooled, the sample is drawn far enough into the capillary to contact chemical reagents disposed therein, if present.

Products of the reaction, if present, can be removed from the capillary by heating the gas near the closed end of in the capillary. Alternatively, the sample drawn into the capillary may be removed from the capillary without a reaction occurring and be delivered to another reaction site, capillary, analytical device or anywhere sample deposition is desired.

In another preferred embodiment, a sample delivery system of the invention is used to introduce a sample into a sample analysis apparatus as disclosed in co-owned, co-pending U.S. patent application Ser. No. 09/(To be amended in when received), entitled "Apparatus And Methods For Sample Analysis" (and identified by Attorney Docket No. SYP-132), which is incorporated by reference herein. A sample analysis apparatus (or sample plug formation device) generally comprises a structure defining two channels which intersect at any angle to form a junction (or "juncture"). One of the channels is a sample introduction channel having an opening for introduction of a sample. The other channel comprises a separation channel, in which may be disposed a medium capable of separating components suspected to be in the sample. The sample analysis apparatus further has means for applying a first pressure differential to the channels so that a sample flows into the junction. Subsequently, a second pressure differential moves a portion of the sample into the separation channel for separation and/or analysis. With the appropriate parameters and control of the pressure differentials, a well defined sample plug can be formed.

Thus, the present invention provides apparatus and methods for rapid, accurate, automated delivery of samples to analytical instrumentation or to chemical reagents for conducting chemical reactions. When used in conjunction with a sample analysis apparatus described above, the reaction and subsequent analysis of a sample can be a fully automated process.

The invention will be better understood upon consideration of the following drawings, description and claims.

DESCRIPTION OF THE DRAWINGS

Like reference characters in the respective drawn figures indicate corresponding parts.

DETAILED DESCRIPTION OF THE INVENTION

Figure 1:
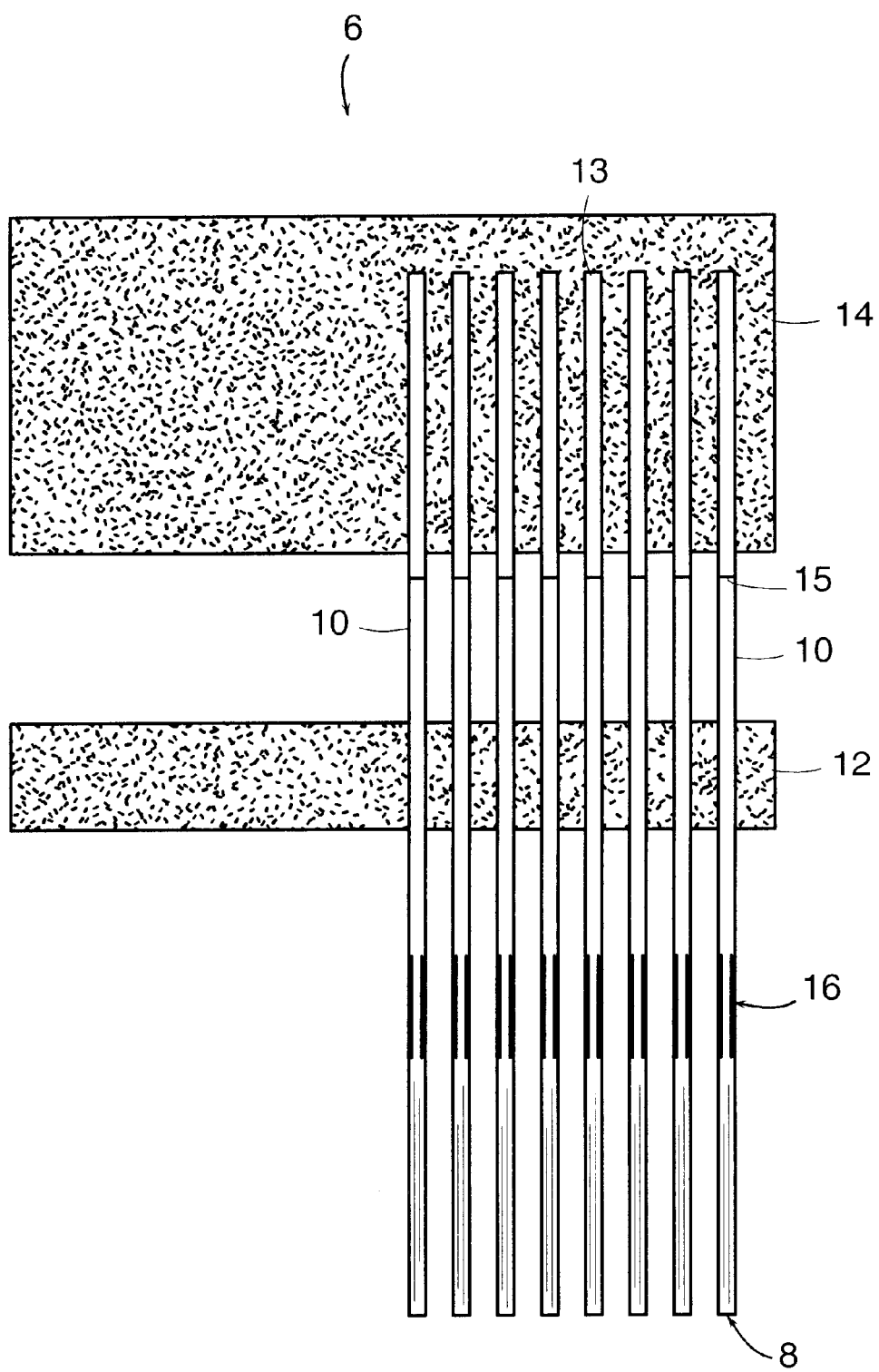
FIG. 1 is a schematic illustration of a cross section of an array of sample delivery systems of the invention with each capillary having reagents for performing chemical reactions disposed therein.

The invention generally provides a sample delivery system for automated delivery of a sample to reagents for conducting chemical reactions and/or to analytical instruments for analysis of microscale samples. As used herein, the term "sample" is intended to mean any source suspected to contain a component to be detected or identified, or any potentially reactive chemical entity. A sample can be "neat" or can be diluted with an appropriate solvent. Currently preferred samples include, but are not limited to, biological specimens suspected to contain a component of interest. Samples suitable for use in the claimed invention include body fluids, such as blood, serum, plasma, urine, cerebrospinal fluid, saliva, sweat, tears, semen, vaginal fluid, amniotic fluid, and ascites.

Broadly, a sample delivery system of the invention comprises a housing defining a channel, such as, e.g., a capillary. The channel has a first end which may be an opening for introduction of a sample, and a second end which is in communication with a volume controller. Typically one end is sealed defining a closed end of the channel. An opening for the introduction of a sample into the channel preferably is opposite the end of the channel in communication with the volume controller, but it may be at any location along the channel.

The volume controller broadly may be a pump, syringe, pipette bulb, thermal regulator or other means for changing the volume and/or pressure in the channel. If the sample delivery system has a closed end, the volume controller preferably is a temperature control device in thermal communication with the closed end of the channel. The temperature control device expands and/or contracts, i.e., heats and/or cools, a thermally expandable fluid located within the channel near the closed end. Regulation of the temperature of a thermally expandable fluid in the channel moves an aliquot of liquid, often containing a sample of interest, into and out of the channel. In this way, a defined amount of sample can be moved a specific distance into the channel then later expelled from the channel.

A sample delivery system of the invention also may have one or more chemical reagents or sets of chemical reagents disposed or immobilized therein. In these embodiments, a sample is delivered to the reagents through the channel for subsequent chemical reaction. If the chemical reaction is conducted at non-ambient temperature, a second temperature control device may be associated with the channel to provide the appropriate reaction conditions. After reaction, the reaction products may be expelled from the channel for further reaction and/or analysis.

Accordingly, a sample delivery system of the invention may be used to conduct numerous types of chemical reactions and/or facilitate analysis of samples. For example, a sample delivery system may be used in diagnostic applications such as blood testing (e.g., to identify blood components, or to detect/identify DNA in blood), immunoassays (e.g., to detect the presence of a specific antigen in a sample), and colorimetric or other assays (e.g. radiochemical, chemiluminescent or binding assays). A sample delivery system of the invention may be used in applications to detect toxins (e.g., bacteria, alcohol, drugs, viruses, organisms, metals, abnormal levels of physiological chemicals, and the like), or other components in a sample (e.g., a biological or environmental sample). In addition, a sample delivery system may be used in chemical synthesis (e.g., in the manufacture of drugs, peptides, nucleotides). A sample delivery system also may be used in numerous laboratory techniques including, but not limited to, peptide or nucleotide sequencing, amplification and/or modification; enzyme screening; and receptor-ligand reaction screening which may use, e.g., an antibody-antigen reaction.

It should be understood that the following discussion and examples will be directed to a preferred thermally-controlled sample delivery system of the invention which uses a capillary as the channel, and a gas as the expandable fluid. That is, e.g., when a gas is referred to herein, its specific reference to one type of thermally expandable fluid and the use of the term "gas" is a representative example of a preferred embodiment used to illustrate the teachings of the invention. However, the same principles and concepts taught by this specification equally apply to the use of any volume controller, channel and/or expandable fluid known to a skilled artisan.

Referring to FIG. 1, an array of sample delivery systems 6 according to the invention is shown. The array of sample delivery systems 6 includes multiple capillaries 10 which are held by an array holder 12. The capillary may be constructed from glass, silicon dioxide (silica), or polymeric materials, either inorganic or organic, such as suitable plastics. The capillaries may be disposable (i.e., single use), or reusable. The capillary surface may be wettable or non-wettable. In another embodiment, the capillary channels are etched or molded into the surface of a substrate. Although a microchip typically has a flat surface which may necessitate multiple extensions and/or joints from the chip, skilled artisans readily will know techniques and materials to fabricate a functional microchip to practice the invention.

The diameter and length of a capillary can vary greatly to provide the necessary dimensions to create the necessary total volume of the capillary. Typical reaction volumes of the invention are less than about 30 microliters ($\mu$L), but preferably are lower. The inner diameter of each capillary typically is in a range of about 5 $\mu$m to about 1000 $\mu$m. The inner diameter of a capillary preferably is between about 20 $\mu$m and 300 $\mu$m. Although dimensions are provided for a substantially circular cross sectional area of a capillary, similar cross-sectional areas are preferred for non-circular channels, e.g., such as rectangular channels having a depth and a width. The open end of the capillary may have a smaller diameter than the rest of the capillary. The capillary also may have an inner diameter which varies a plurality of times along its longitudial axis to provide various "zones" along the capillary. Although microscale size samples are preferred and described, this in no way limits the invention since large scale sample delivery may be accomplished using the principles and concepts disclosed herein.

Again referring to FIG. 1, one end of each of the capillaries 10 is sealed defining a closed end of the capillary 13. The closed end of the capillary 13 is associated with and in thermal communication with a temperature control device 14. However, the temperature control device 14 does not need to encompass the whole of the closed end 13 as depicted in FIG. 1. The temperature control device 14 may be any heating/cooling element capable of heating or cooling gas in the capillaries 10, e.g., a thermoelectric heater. The temperature control device 14 also may be or include a thermally controlled fluid such as water or polyethylene glycol which may circulate through a constant temperature bath.

Preferably, the temperature control device is capable of reaching a preselected temperature within a particular time frame. The temperature control device also preferably is capable of maintaining the preselected temperature within a tolerance range of a particular reaction for the required length of time. Thus, the temperature control device can be any suitable commercially available or custom made heating and cooling device which is capable of attaining temperatures required to expand and contract the thermally expandable fluid within a channel. The particular thermally expandable fluid used to practice the invention will dictate the necessary temperatures the temperature control device needs to achieve.

A temperature control device also may include an auxiliary controller such as any suitable microprocessor based programmable logic controller, personal computer controller, or the like for process control. A suitable controller includes features such as programmability, reliability, flexibility, and durability. The suitable controller includes various input/output ports used to provide connections to regulate the temperature control device as well as open and close valves, regulate and meter fluids, among other features. The controller also includes sufficient memory to store process recipes for desired application. Of course, the type of controller used depends upon the particular application.

A sample delivery system of the invention may include an insulator partition 15 as shown in FIG. 1. The insulator partition 15 essentially separates the thermally expandable fluid near the closed end of the capillary 13 from the "reaction zone," which is the area within the capillary between the insulator partition 15 and the open end of the capillary 8. The phrase "reaction zone" generally refers to the areas of the capillary in which reaction reagents are present, reactions are conducted, and reaction solvents or mixtures come into contact. In preferred embodiments where the expandable fluid is a gas, the insulator partition is gas permeable. The insulator partition may be stationary or movable, and rigid or flexible, depending on the materials of construction for the partition and the particular application.

Use of an insulator partition assists in maintaining the thermally expandable fluid near the closed end of the capillary at a temperature independent from the remainder of the capillary so movement of sample within the capillary is controlled substantially by the temperature control device. In this way, a reaction may be conducted at nearly any temperature in a discrete location of the capillary without movement of the reaction liquid volume due to expansion or contraction of the thermally expandable fluid.

An insulator also may be exterior of the capillary and in thermal communication with it. The exterior insulator may be any suitable material which has high thermal conductivity appropriate for the particular application. The exterior insulator also may be in thermal communication with other materials which dissipate temperature. An exterior insulator also may be used in conjunction with an insulator partition.

Referring to FIG. 1, a sample delivery system of the invention may further contain one or more chemical reagents 16 disposed within or immobilized on the inner walls of the capillaries 10. Immobilization of the chemical reagents 16 may be accomplished by drying on the interior of the capillary walls. Reagents 16 may be delivered into the capillary 10 by many methods, e.g., injecting them using a microneedle. After the chemical reagents 16 are in the desired location within the capillary 10, the reagents 16 may be dried, e.g., by heating, desiccating or vacuum drying the capillary 10 under appropriate conditions so the reagents 16 remain at their site of deposition. One or more of these drying techniques may be combined to dry the reagents 16, to the walls. The chemical reagents 16 also may be immobilized within the capillary 10 by absorbing them into a bulk material, such as cotton, which is placed in the capillary. In addition, certain chemical reagents 16, such as PCR reagents, may be dried in an appropriate matrix, e.g., dextran or trehalose, prior to immobilization on the capillary walls.

More than one chemical reagent simultaneously may be present in a capillary. That is two or more chemical reagents may be in the same reaction zone thereby defining a set of chemical reagents. However, the two or more chemical reagents independently may be spaced apart from each other within the capillary. It should be understood that the use of the term "set" in describing the chemical reagents is intended to define one or more groupings or associations of chemicals reagents and is not intended necessarily to mean more than one reagent.

Each set of chemical reagents preferably is dried in separate rings around the capillary walls. Relative placement of the reagents depends on many factors. That is, the dimensions of the capillary and the liquid volume of the reaction affect the placement of the reagents. In addition, the reaction conditions, including temperature and amount of reactants needed for reaction or analysis, influence the placement of the reagents in the capillary. Moreover, the sequence of reactions to be conducted affects the placement of reagents since contact of sample with immobilized reagents will occur sequentially as the sample moves in the capillary from the open end to the closed end then back out the open end.

Reagents useful in the invention may be any chemical entity which potentially interacts with a sample or component thereof Since the apparatus and methods of the invention are useful in a plethora of chemical interactions, the reagents useful in the invention only are limited by the knowledge of one skilled in the art. Accordingly, reagents include, e.g., a binding protein, a nucleic acid probe, a PNA probe, an enzyme, a substrate, a ligand, a receptor, an antibody and/or an antigen. Reagents additionally may include buffers, stabilizers, surfactants, additives, excipients, carriers, haptens, or other compatible molecules that facilitate or influence reaction with sample components. Reagents may be labeled for detection with a detectable moiety or label, or for property modification. Preferred detection labels include, but are not limited to, fluorescent, chemiluminescent, radioactive, mass spectrometry, and colorimetric labels. Preferred property modification labels include, but are not limited to, charge modification labels which can alter the electrophoretic mobility of a reagent, and biorecognition or chemical recognition labels which facilitate enhanced analytical selectivity.

Probes useful in a sample delivery system may be any nucleotide binding compound, such as, e.g., a riboprobe, a polynucleotide, or a PNA. Preferably the probe is complementary to a target sequence present in the sample. In certain embodiments, probes also may be binding proteins or other synthetic constructs. It is preferable that the probes are detectably labeled. Preferred labels include radioisotopes, fluorescent or colorimetric labels, enzymatic labels, and molecular weight labels, as well as other useful labels known to those skilled in the art.

A particularly preferred probe is a peptide nucleic acid (PNA). PNAs are DNA mimics with a neutral polyamide backbone on which the nucleic acid bases are attached in the same manner as they are attached to the phosphate backbone of DNA. See, e.g., Egholm, et al., *Nature*, 365: 566–568 (1993); Oerum, et al, *Nucl Acids Res.*, 23: 5332–36 (1993); *Practical PNA: Identifying Point Mutations by PNA Directed PCR Clamping*, PerSeptive Biosystems Vol. 1, Issue 1 (1995). See, also, PCT publications EP 92/01219, EP 92/01220, and U.S. Ser. No. 92/10921, which are herein incorporated by reference. Peptide nucleic acid probes typically form more stable duplexes with DNA as compared to DNA/DNA duplexes. Additionally, because PNA/DNA complexes have a higher thermal melting point than the analogous DNA/DNA duplexes, use of PNA probes can improve the reproducibility of blotting assays. Peptide nucleic acid synthons and oligomers are commercially available. (PerSeptive Biosystems, Inc., Framingham, Mass.).

As used herein, the term "detectable moiety" is intended to mean any suitable label, including, but not limited to, enzymes, fluorophores, biotin, chromophores, radioisotopes, colored particles, electrochemical, chemical-modifying or chemiluminescent moieties. A currently preferred detectable moiety is a fluorescent moiety. Common fluorescent moieties include: fluorescein, cyanine dyes, coumarins, phycoerythrin, phycobiliproteins, dansyl chloride, Texas Red, and lanthanide complexes. Of course, the derivatives of these compounds which are known to those skilled in the art also are included as common fluorescent moieties.

Property modification labels include, but are not limited to, charge modification labels which can alter the electrophoretic mobility of a reagent, and biorecognition or chemical recognition labels which facilitate enhanced analytical selectivity. Preferred property modification labels are mass modification labels such as mass tags. Preferred charge modification labels are known in the art, e.g., see U.S. Pat. No. 5,630,924 which is herein incorporated by reference.

Figure 2:
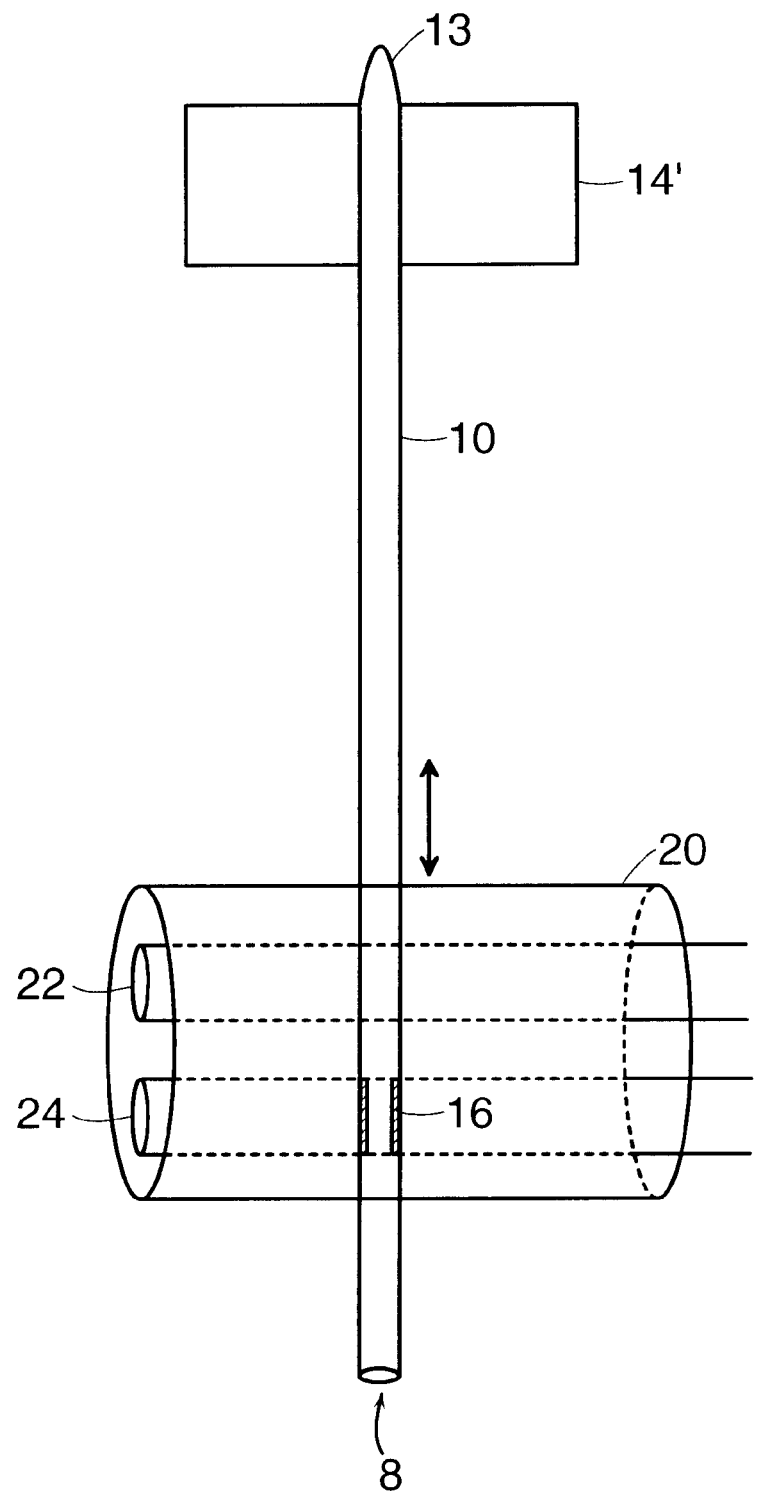
FIG. 2 is a schematic illustration of a cross section of a preferred sample delivery system of the invention comprising a capillary, a first temperature control device and a second temperature control device.

Referring to FIG. 2, another embodiment of the invention includes a second temperature control device 20 in thermal communication with a capillary 10. The sample delivery system shown in FIG. 2 also has a first temperature control device 14' associated with the closed end of the capillary 13. The second temperature control device 20 typically is located closer to the open end of the capillary 8 than the first temperature control device 14. The illustrated second temperature control device 20 has two conduits 22 and 24 for regulating the temperature of the capillary 10 in the discrete zone where each conduit thermally communicates with the capillary 10.

For example, as shown in FIG. 2, conduit 24 is positioned to regulate the temperature of the capillary where the chemical reagents 16 are immobilized. The invention may be practiced by keeping the second temperature control device 20 stationary and using the first temperature control device to move the sample or reaction mixture to the zone (or zones) in communication with conduits 22 and 24. In these embodiments, one of the first conduit 22 or second conduit 24 can maintain a first temperature and the other of the conduits can maintain a second temperature. However, in certain preferred embodiments, e.g., in a PCR process, the reaction mixture preferably remains stationary in the capillary during the entire reaction process, i.e., thermocycling occurs in the zone where the PCR reagents are immobilized. In these embodiments, the second temperature control device 20 can remain stationary or can move along the longitudial axis of the capillary 10.

In the first case, where the second temperature control device 20-remains stationary, the second conduit 24 usually is positioned in thermal communication with the zone of the capillary 10 where the chemical reagents 16 are located as depicted in FIG. 2. The second conduit 24 is used to regulate and maintain the temperature or temperatures which are required during a reaction or reactions, e.g., thermocycling.

That is, a heated liquid or gas can be passed through the second conduit 24 to heat the reaction liquid volume, then a cooler liquid or gas can be passed through the second conduit 24 to cool the reaction mixture. In this way, thermocycling of the reaction mixture (also called "reaction solution" or "reaction liquid volume") is achieved. Using this technique permits the first conduit 22 to act as an insulator for the closed end of the capillary 13, e.g., by flowing a constant temperature fluid through the first conduit 22. In other words, the first conduit 22 may be used as an insulator to maintain the thermally expandable fluid in the sealed end of the capillary 13 at a constant temperature thereby ensuring the reaction mixture remains essentially stationary throughout the reaction process.

In the second case, where the second temperature control device 20 moves along the longitudial axis of the capillary 10, each of the first conduit 22 and second conduit 24 independently can maintain a distinct temperature within their respective zones of thermal communication with the capillary 10. As a result, the reaction mixture can remain stationary and the second temperature control device 20 moves to provide a first temperature with conduit 22 and a second temperature with conduit 24. It should be understood that although two conduits are discussed and depicted, a second temperature control device 20 of the invention may have any number of conduits to provide the various temperatures and/or insulating features discussed above. Moreover, a second temperature control device also may have more than 2 conduits.

Figure 3:
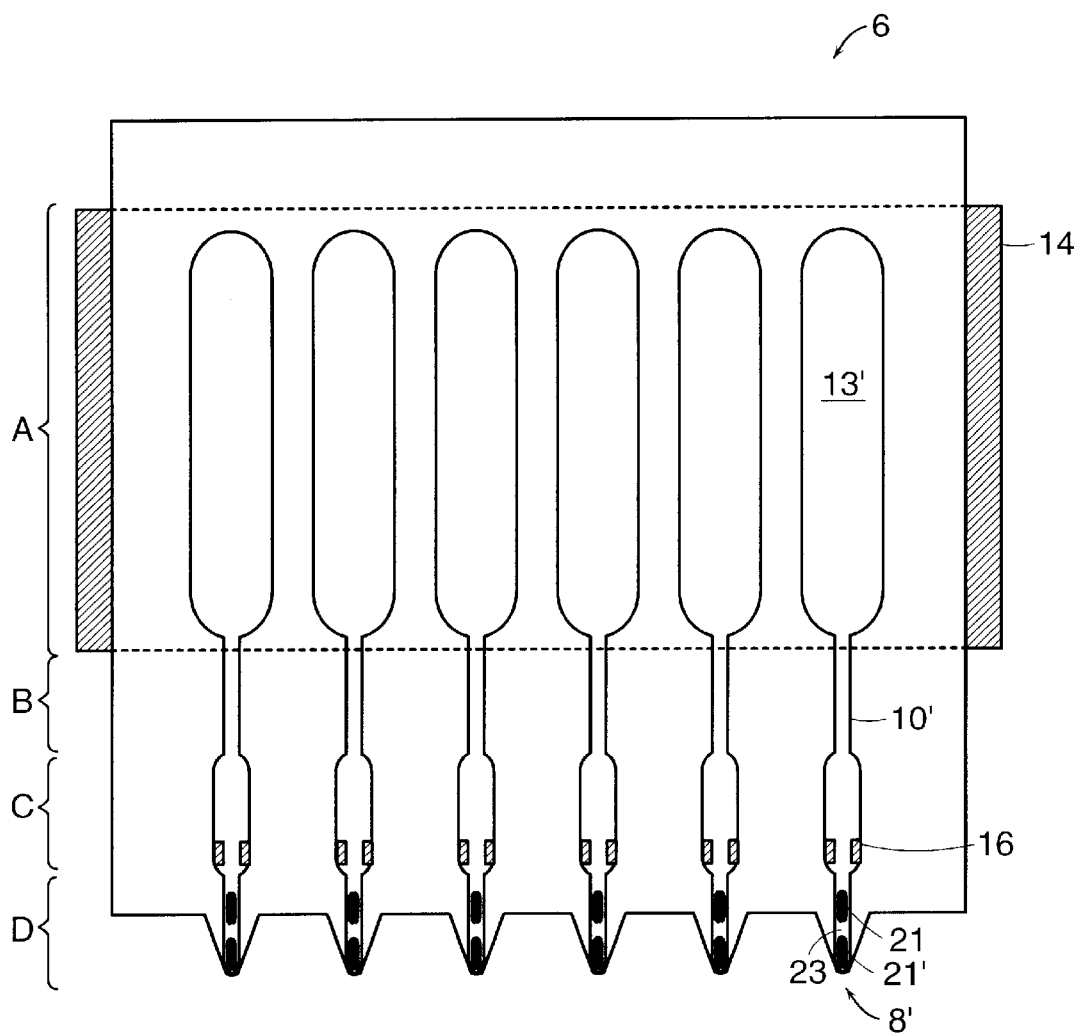
FIG. 3 is a schematic illustration of a cross section of an array of preferred sample delivery systems of the invention comprising microfabricated channels, each having an inner diameter which varies along its longitudinal axis.

FIG. 3 illustrates a cross-sectional view of a preferred embodiment of the invention which is an array of microfabricated sample delivery systems. The channels are formed on a microfabricated solid, such as, e.g., a glass or plastic substrate, which may be in the form of a microchip. The channels typically are etched or molded into the surface of the solid substrate as discussed below. As depicted in FIG. 3, the channel 10' has an inner diameter which varies a plurality of times along its longitudial axis. Consequently, the channel has various zones (or regions) which permit isolation of different functions and/or reactions.

For example, in FIG. 3, the zone of channel 10' referenced as letter "A" is the thermal control region of the channel. This region includes the closed end of the channel 13' which is in thermal communication with a temperature control device 14. In the illustrated embodiment, the temperature control device 14 is a thermally regulated layer which is in thermal communication with the entire thermal control region "A" of the channel 13'. As depicted, the thermally regulated layer is behind the channels. However, the layer preferably is in front of the channels (or on top if the channels are horizontal). In addition, multiple layers may be used. The layer may be directly in thermal communication with the channels or may be in thermal communication with a substrate cover (not shown). Typically, the thermally regulated layer is a heat sink which is coupled to an appropriate thermal regulator which modulates the temperature of the fluid in the closed end of the channel.

The zone referenced as letter "B" is a thermal isolation region where the channel 10' is constricted to help thermally insulate the thermal control region from the sample and/or reagents. Zone "C" is the reagent mixing and incubation region, or "reaction zone." In this region of the channel 10', a sample may react with chemical reagents 16 which are optionally present. This region also may be used to mix reagents and/or sample which have been introduced to the channel via multiple introductory subchannels (not shown) or via "bubble segregation" (to be discussed further below).

Zone "D" is the introduction region where sample and/or reagents are supplied to the interior of the channel for transport therein. The channel in this region often is of a smaller diameter than the majority of the channel. The channel in zone "D" also may include multiple open ends and introductory subchannels which converge at or near the reaction zone for mixing and the like therein.

Microchips having channels can be designed and fabricated in large quantities from a solid substrate material which easily can be sterilized. Silica is a preferred substrate material because of the well-developed technology permitting its precise and efficient fabrication, but other materials may be used, including polymers such as polytetrafluoroethylenes. The channels may be fabricated inexpensively in large quantities from a silica substrate by any variety of micromachining methods known to those skilled in the art. The micromachining methods available include film deposition processes, such as spin coating and chemical vapor deposition, laser fabrication or photolithographic techniques, such as UV or X-ray processes, or etching methods, which may be performed by either wet chemical processes or plasma processes. (See, e.g., Manz, et al., *Trends in Analytical Chemistry* 10:144–149 (1991).) However, other fabrication approaches may be used.

Channels of varying widths and depths can be fabricated with microscale dimensions. Micromachining also provides a simple means to permit a plurality of channels to be fabricated and interrelated, i.e., in fluid communication with one another. It should be understood that a channel of the invention may not have a consistent longitudial axis. That is, a channel may have multiple open ends to permit the introduction of multiple samples and/or reagents to the channel. In addition, a channel of the invention may have a closed end which is in communication with multiple other channels thereby providing a common closed end which in conjunction with a temperature control device which concurrently facilitates movement of liquid in the channels. Accordingly, many various designs and layouts of channels are possible depending on the particular application. Of course these same design principles apply to capillaries. However, complex designs preferably are micromachined.

The channels may be enclosed using techniques known in the art. For example, the channels may be enclosed by bonding another flat substrate over the etched or impressed side of the microfabricated substrate. If the enclosing substrate is thin, it will transfer heat rapidly, even if it is composed of a thermally insulating material. Preferred thin film materials for enclosing microfabricated features include, but are not limited to, polyimide (e.g., Kapton®), Mylar (e.g., MonoKote), polyethylene, Teflon, glass, and laminates and composites of these materials. If desired for the application, reagents may be deposited and dried onto the walls of the channel prior to enclosing the channels.

The width and depth of a microfabricated channel can be adjusted to facilitate functions such as solution mixing, solution segregation, thermal isolation, and interchannel manifolding. Additionally, multilayered microfabricated sample delivery systems can increase the functionality of the sample delivery system through integration of other channel structures or integrated electronic devices through methods known to those in the art. Registration features also may be imprinted into the substrate to facilitate assembly and robotic handling functions.

Moreover, the silica substrate containing fabricated channels may be covered and sealed with a thin anodically bonded glass cover. Other clear or opaque cover materials may be used. Alternatively, two microfabricated silica substrates can be sandwiched, or a silica substrate can be sandwiched between two glass covers. The use of a transparent cover results in a window which facilitates dynamic viewing of the channel contents and allows optical probing of the channels either visually or by machine.

The use of microfabricated channels in a solid substrate as described above provides many advantages. The dimensions and shape of the channels may be adjusted for processes or functions not easily accommodated using single-diameter capillaries. For example, solutions drawn into a channel which initially are segregated by a bubble may be mixed if the solutions are transported to a region of the channel which has an enlarged diameter. Alternatively, channels may be fabricated with reduced diameter areas so as to decrease the rate of heat transfer from one section of the channel to another.

In addition, microfabricated channels permit a reagent solution to be disposed easily in a region of an unenclosed channel and subsequently dried to leave the reagent within the channel prior to enclosing the channel with an enclosing substrate. Moreover, multilayered microfabricated structures may be formed which increase the functionality of the sample delivery system through channel manifolding or through integration of electrical components into the sample delivery system using methods known to those in the art. In other embodiments, registration features may be etched or molded onto the substrate to permit alignment of the substrate with other instrument components or other layers of the sample delivery system thereby simplifying the alignment and handling of the substrates in an automated robotic system. All of the above features assist in reducing the complexity of the delivery system of the invention by providing a single solid delivery system containing an array of channels which may be handled easily and efficiently.

Figure 4:
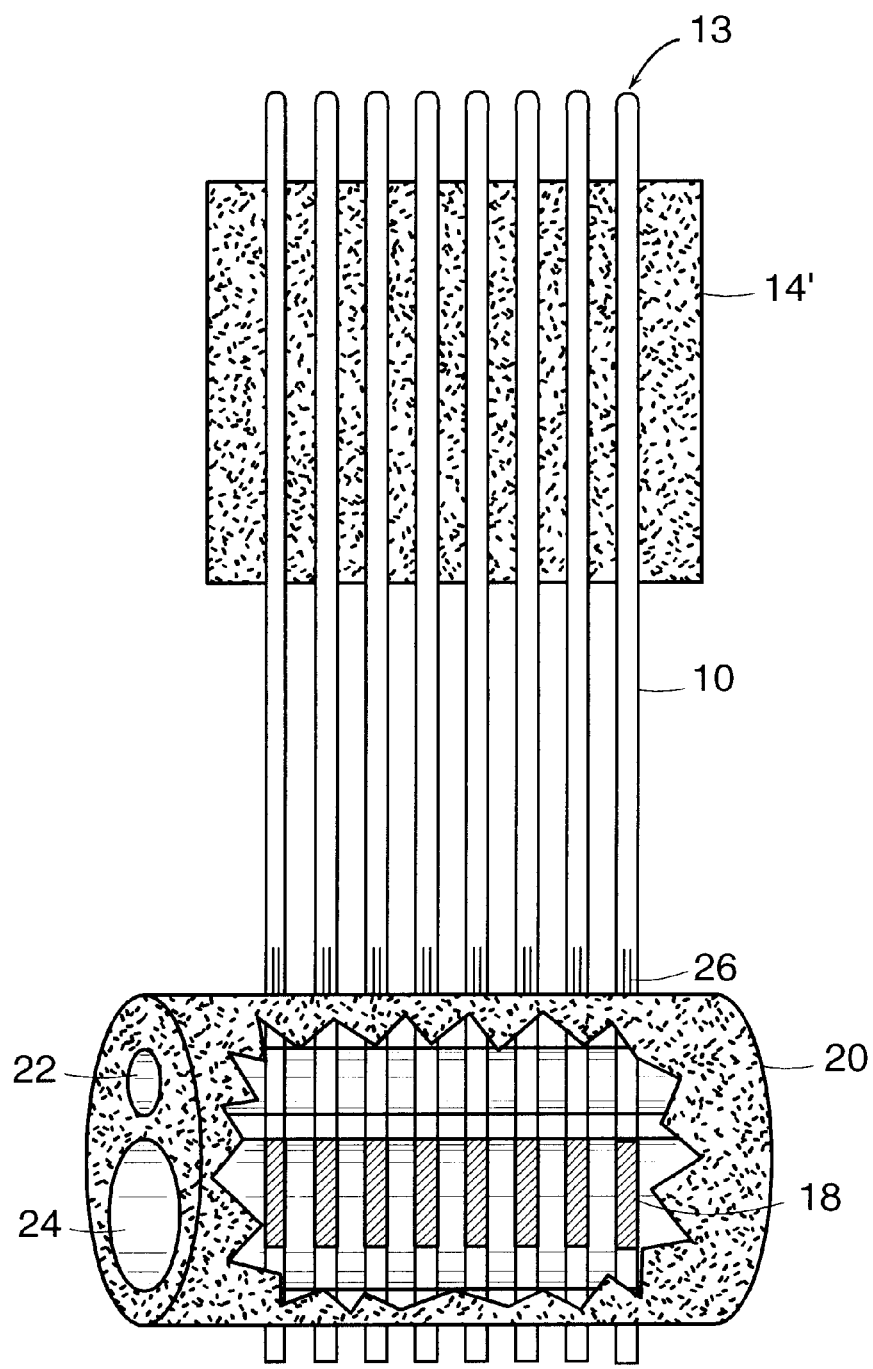
FIG. 4 is a schematic illustration of a cross section of an array of preferred sample delivery systems of the invention comprising capillaries associated with a first temperature control device and a second temperature control device.

FIG. 4 shows an array of capillaries 10, each having a closed end 13 and each being in association with a first temperature control device 14'. The capillaries 10 each contain a first set of chemical reagents 18 and a second set of chemical reagents 26 immobilized on the capillary walls. A second temperature control device 20 comprising conduits 22 and 24 for heating and/or cooling, respectively, permits control of the temperature in the discrete portion of the capillary containing the chemical reagents as discussed above. Use of the second temperature control device and an insulator (e.g., an insulator partition, not shown) allows for the temperature of the reactions to be controlled without thermally affecting the gas in the closed end of the capillary.

In its broadest aspect, methods of the invention are directed to using a sample delivery system described above to charge an aliquot of a sample to a desired location. The volume of fluid in a capillary is modulated by the temperature of the fluid in the capillary. Preferably, the fluid is a gas. However, the fluid may be an inert liquid. Regardless, the volume and pressure of the thermally expandable fluid is the means used to move a sample into and out of the capillary.

Figure 5:
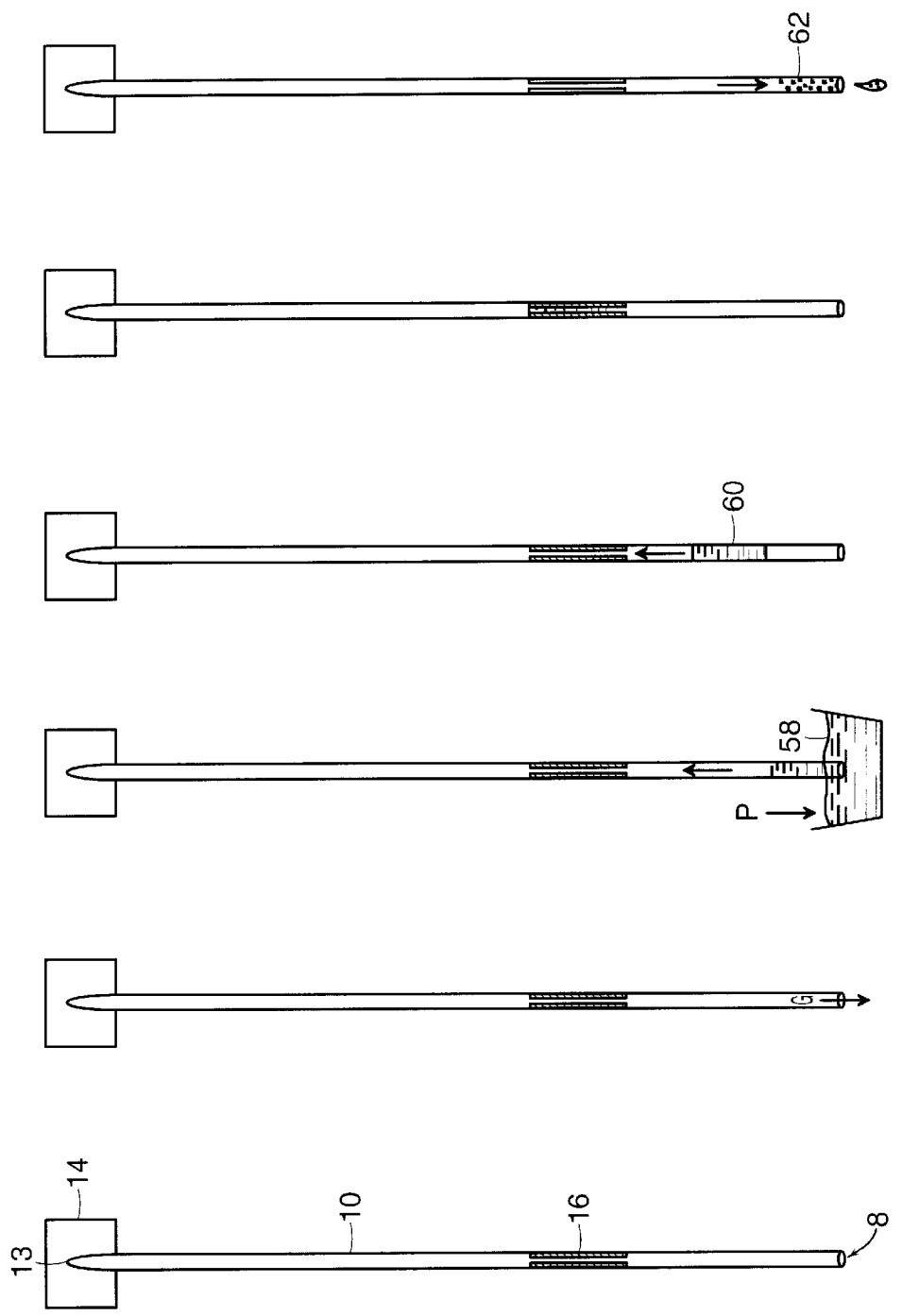
FIGS. 5:A–F are schematic illustrations of a cross section of a sample delivery system of the invention during practice of the invention.

FIGS. 5A–5F depict the various stages of a sample delivery system during the practice of a method of the invention. FIG. 5A shows a sample delivery system of the invention prior to use and similar to the system depicted in FIG. 1. Changing the temperature of a thermally expandable gas in the capillary causes that gas to expand or contract. Typically, when a gas is heated, the volume it occupies, and hence the pressure in the capillary, increases approximately according to the perfect gas law PV=NRT, where P is the pressure, V is the volume, n is the number of gas molecules, R is the constant 8.314 JK$^{-1}$ mol$^{-1}$, and T is the temperature in degrees Kelvin. When the gas is heated by the temperature control device 14, and one end of the capillary is sealed 13, the expanding gas ("G") will escape through an opening in the capillary 8 following the path of least resistance as shown in FIG. 5B. Accordingly, the pressure in the capillary 10 is lowered. Subsequently, the capillary 10 is submerged in a sample 58 (FIG. 5C) and the gas cooled. The pressure differential between the outside and the inside of the capillary 10 forces an aliquot of sample 60 into the capillary 10. That is, the pressure outside the capillary 10, represented by the letter "P" in FIG. 5C, "pushes" on the sample 58 to equilibrate the pressure inside and outside the capillary 10. As shown in FIG. 5D, after cooling, an aliquot of sample 60 is introduced into the capillary 10.

Preferably, the volume of sample charged into the capillary is a preselected or metered aliquot which typically is determined by the amount of time the capillary 10 is immersed in the sample 60 and the pressure differentials acting on the sample. Subsequently, the aliquot of sample 60 which is drawn into the capillary may be deposited elsewhere for further reaction and/or analysis (not shown).

Alternatively, the sample and reagent solutions may be introduced and/or metered into a capillary by non-thermal means. For example, an ancillary volume control device in fluid communication with a capillary may be used to introduce a predetermined aliquot of solution into the capillary. Another example is the use of capillary action to fill a portion of a capillary. With the proper design, a predetermined amount of solution may be introduced into the capillary via capillary action to provide a metered aliquot. Moreover, with a capillary having multiple open ends and introductory subchannels, multiple solutions may be introduced to a capillary simultaneously and in metered amounts. Subsequent to the solution entering the capillary, thermally actuated volume changes in the capillary as discussed above may be used to transport the sample and/or reagents to other regions of the capillary.

In certain preferred embodiments, as depicted in FIGS. 5A–5F, an aliquot of sample 60 may be drawn into the capillary 10 so that the aliquot of sample 60 is delivered to and contacts a chemical reagent 16 which is pre-loaded in the capillary 10. Upon contact of the aliquot of sample 60 with the chemical reagent 16, if the conditions are appropriate, a chemical reaction may occur as shown in FIG. 5E. To facilitate a reaction or interaction, the reaction conditions may be changed using a second temperature control device (not shown) as described above, i.e., by heating or cooling that area of the capillary where the reagent 16 is located. Subsequent to reaction, reaction products 62 and other components such as starting materials may be eluted from the capillary 10 to an appropriate location by increasing the temperature of the gas near the closed end of capillary 13 as described above and depicted in FIG. 5F.

Alternatively, with the appropriate system and application, the reaction products 62 may be moved to another zone of the capillary by heating or cooling the gas near the closed end of the capillary 13 using the temperature control device 14. In another zone, the reaction products 62 may be directly analyzed in the capillary, or may contact a second chemical reagent for potential further reaction under the proper conditions. It should be understood that if no reaction between the sample and reagents occurs, the sample may be moved and/or analyzed as above to provide useful information the same as if a reaction had occurred.

Another technique which can be practiced using a sample delivery system of the invention is known as "bubble segregation." An aliquot of an initial sample is drawn into a capillary, the capillary is withdrawn from the initial sample and then placed into a second sample. The second sample may be a solution of reagents. Upon further cooling of the gas trapped in the capillary near the closed end, the second sample (or reagents) is drawn into the capillary and begins to mix with the initial sample at their interface. Depending on many factors, the mixing of the two samples may be controlled. However, the introduction of the second sample into the capillary can occur subsequent to a volume of gas first being drawn into the capillary which would create a "bubble" between the first sample and the second sample. This is "bubble segregation" since an air bubble separates the two liquids drawn into the capillary and prevents their mixing. Accordingly, based on the aforementioned techniques and others known to skilled artisans, a variety of useful procedures can be designed and implemented to suit the particular requirements of an experimental protocol or application.

For example, if the bubble-segregated solutions (either samples and/or reagents) are transported to a region of the capillary where the capillary diameter increases, the bubble will no longer form an effective barrier between the two solutions and the solutions will contact each other and be free to mix. This application of "bubble segregation" is depicted in FIG. 3. As shown, a first solution 21 was introduced to the open end of the channel 8', followed sequentially by a gas and a second solution 21'. The result is a gas bubble 23 which segregates the first solution 21 from the second solution 21'. Subsequently, as the solutions and bubble move along the longitudinal axis of the channel away from the open end 8', they will enter the reaction zone ("C") where the bubble will no longer be effective to segregate the solutions due to the increased volume of the channel 10' in that region. Consequently, the solutions will contact each other, as well as the chemical reagents 16 optionally disposed therein.

To assist in automating the methods described herein, another aspect of the invention is a scientific instrument which contains the sample delivery systems described above. The scientific apparatus permits the efficient automation of the systems of the invention with its auxiliary devices and equipment. The scientific apparatus also permits other apparatus to be linked to the delivery systems of the invention to allow a functional design to suit the end users needs. For example, analytical instruments may be linked to a scientific instrument of the invention to permit analysis of samples, e.g., at given times in the reaction cycle. Analytical instruments useful in the invention will be well known to those skilled in the art and include, but are not limited to, mass spectrometry instruments, chromatography systems, and various detection instruments such as ultraviolet, infrared, fluorescent, and refractive indices detectors.

Other non-limiting examples of auxiliary instruments useful in the invention include diagnostic instruments for performing assays, and synthesizers for automating the production of particular compounds to become part of a sample. Such synthesizers include those capable of performing combinatorial syntheses which permit the screening of libraries of compounds with the delivery systems of the invention. All of the above instruments and devices may be operated manually in a step-wise fashion. However, full automation is preferred. As appreciated by a skilled artisan, automation preferably includes a microprocessor and/or computer which controls various aspects of the methods of the invention, but typically at least is in communication with the temperature control device.

Having disclosed the basic operation and principles underlying the invention, a skilled artisan readily would recognize various sample delivery and chemical reaction schemes/protocols which may be used in conjunction with this invention. For example, there may be multiple reactants present in the capillary, each separated by an inert zone. The variation of temperatures of reaction may be controlled by multiple temperature controllers located adjacent each set of reactants or a second temperature controller having multiple conduits positioned accordingly. Thus, a variety of chemical reactions and processes may be facilitated by or carried out in the sample delivery system of the invention, including, but not limited to, PCR.

A sample delivery system of the invention may be used to deliver a sample, a reacted sample and/or other reaction products to an apparatus for analysis. A particularly preferred apparatus is described in co-owned U.S. Pat. No. 6,375,817, entitled "Apparatus And Methods For Sample Analysis," which is herein incorporated by reference in its entirety. The above-referenced sample analysis apparatus (or sample plug formation device) has a housing defining two channels which intersect to form a junction which facilitates formation of a sample plug. Subsequent to its formation, the plug of sample is transported along one of the channels, a separation channel, to an analytical instrument, and/or to separate the sample into its individual components prior to detection.

Figure 6:
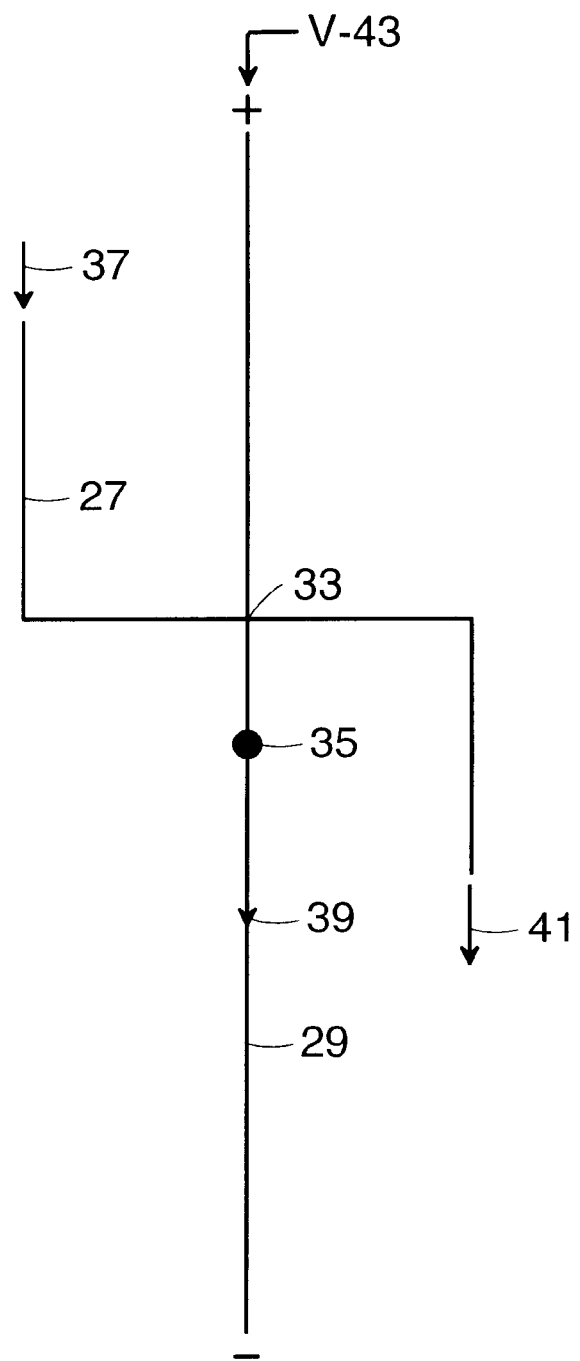
FIG. 6 is a schematic illustration of a sample analysis apparatus (also called a sample plug formation device) having a sample introduction channel and a separation channel.

As shown in FIG. 6, a first channel for introduction of a sample is a sample introduction channel 27, and a second channel which intersects the sample introduction channel 27 is a separation channel 29. The apparatus further comprises a means for generating pressure differentials on the channels, such as a vacuum pump or peristaltic pump. The apparatus also may comprise a voltage generator 43 for generating a voltage gradient along the separation channel 29. Finally, the apparatus may comprise a detector for detecting components in the separation channel.

As stated above, in a preferred embodiment, the channels are formed on a microfabricated solid, such as, e.g., a silicon dioxide or silica substrate, which may be in the form of a microchip. Each channel typically contains an appropriate medium. The separation channel may have a medium for separating sample components based on their charge or size. The medium may comprise, e.g., sieving media, such as polyacrylamide. However, other sieving media for a particular application may be used as recognized by a skilled artisan. Accordingly, a sample delivery system used in conjunction with a sample analysis apparatus may be used to perform complex reaction, separation and analysis protocols, e.g., immunoassays or polynucleotide identifications.

An apparatus for analysis used in conjunction with a sample delivery system of the invention provides for the automated, uniform preparation of sample plugs through the use of vacuum and/or pressure on the sample introduction and separation channels. As illustrated in FIG. 6, the sample introduction channel 27 forms a junction 33 with the separation channel 29. Applying pressure and/or vacuum to the sample introduction channel 27, then the separation channel causes a sample plug 35 to form downstream of the junction 33 in the separation channel 29. (It should be understood that FIG. 6 is a schematic representation and that in practice, the sample plug 35 is contained within the channels.) Arrows 37, 39, and 41 show the direction of sample flow. Voltage generator 43, if present, may apply a voltage gradient axially along the separation channel. A voltage gradient may be applied while a pressure gradient moves sample along the sample introduction channel past the junction to practice one type of sample plug formation technique referred to as "stacking." Using a stacking technique, a dilute sample may be concentrated prior to separation and/or analysis.

Figure 7:
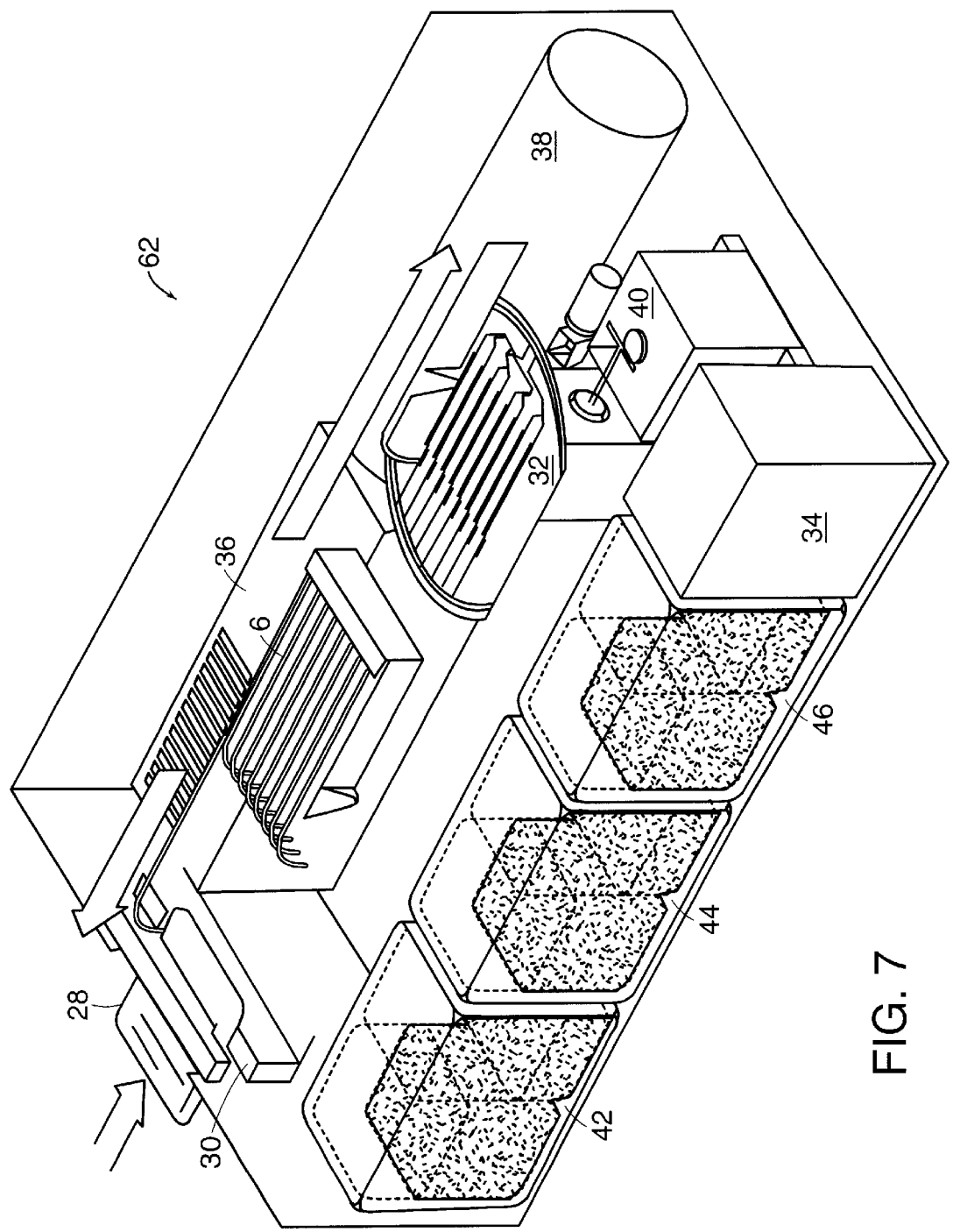
FIG. 7 illustrates an integrated sample delivery system and sample analysis apparatus for rapid, automated sample preparation and analysis.

A sample delivery system of the invention, used in conjunction with a sample analysis apparatus described above, provides for the rapid, automated analysis of biological samples without the complex machinery, time and biohazard exposure inherent in the use of existing systems. FIG. 7 shows an integrated sample analysis apparatus and sample delivery system array. The integrated device 62 contains a sample card 28 having a platform or membrane onto which a sample, such as blood, is deposited. The card may be, e.g., an IsoCode™ card (Schleicher & Schuell, King, N.H.). The integrated device 62 further includes an array of sample delivery systems of the invention 6, as described above. The device 62 contains a microchip assembly 32 having sample introduction and separation channels, which are connected to pressure/vacuum unit 34, high voltage power supply 36, and high pressure cartridge 38.

Near the end of the microchip assembly's separation channels is an optical scanning module 40. The optical scanning module detects the presence of detectable moieties bound to the component of interest in the sample. Detection can be achieved by methodologies including, but not limited to, absorbance of ultraviolet radiation, absorbance of visible radiation, fluorescence, refractive index, Raman or mass spectrometry, electrochemistry, and/or conductivity. Detection by fluorescence is preferred. Fluorescence detection using this module involves a microchip laser beam, which scans across the channels of the microchip 32. The module may detect fluorescence using confocal optics.

The integrated device 62 may further include a sterile deionized water unit 42, a sieving gel buffer unit 44, and a micro-channel reconditioning solution unit 46. As shown in FIG. 7, each of these three units is divided into two halves with one half containing the fresh solutions and the other half containing waste solutions.

In operation, a sample is deposited onto the membrane of the sample card 28, and the card is inserted into the integrated device 62. In this example, the cells in the sample are lysed by the chemical reagents contained in the membrane. The cellular DNA, or other sample components, are then dried onto the membrane by heating with oven 30. At this point the card can be removed and archived, or it can be used in continued processing. Alternatively, a Guthrie paper dried blood blot may be used to deposit the sample.

After drying of the sample to the card, the card membranes are steam heated using sterile deionized water from unit 42 so as to extract the sample components into a small quantity of liquid. As described above, the closed ends of the capillaries of the array of sample delivery systems 6 are heated to expel gas, moved into position over the membranes, and dipped into the liquid containing the sample. Upon cooling of the closed ends of the capillaries, the gas in the capillaries contracts and sample is drawn into the capillaries. The capillaries are preferably pre-loaded with the reagents specific for the immunoassay or polynucleotide detection to be performed, as mentioned above.

After an appropriate reaction time, the reaction products are deposited in the sample introduction channels of the microchip assembly 32. The array of sample delivery systems 6 typically moves to position the open end of the capillaries above the sample introduction channels. The closed ends of the capillaries then are heated by temperature control device so that gas trapped inside the capillary expands and forces sample out of the capillary, as described above. After use, the array of sample delivery systems 6 may be disposed of and new delivery systems containing reagents for the next reaction of interest may be inserted into the integrated device 62. With the appropriate conditions and application, a fresh array of sample delivery systems 6 may be introduced to the integrated device 62 by rolling off a spool and cutting to a desired length.

Subsequent to deposit at the sample introduction channel of the microchip assembly, a pressure/vacuum unit 34 manipulates the pressure gradients inside the sample introduction and separation channels of the microchip, thereby moving a portion of the sample, i.e., a sample plug, into the separation channel. Application of pressure along the separation channel essentially results in formation of a plug of sample in the separation channel downstream of the junction as previously shown in FIG. 6.

If separation involves electrophoresis, after formation of the sample plug in the separation channel, voltage generator 36 is used to apply a voltage gradient axially along the separation channel of the microchip 32 to separate the components of the sample. A sieving medium is pre-loaded into the channels of the microchip. The buffer from unit 44 is injected into the separation channels prior to formation of the sample plug.

As the samples reach the end of the separation channel, optical scanning module 40 scans the separation channels to detect the presence of the detectable moieties attached to the sample components by reaction with the chemical reagents contained in the array of sample delivery systems 6. For polynucleotide identifications, the results of the optical scanning are compared against data produced from genotyping experiments. This data is in the form of intensity vs. time graphs that are electronically searchable in determining matching similarity.

After performance of the analysis, pressure from high pressure cartridge 38 is used to apply pressure at both ends of the separation channel to cleanse the channels of the microchip assembly. The channels are then reconditioned using reconditioning solution from unit 46. The microchip assembly then may be reused in subsequent analyses. Alternatively, the microchip assembly may be disposed of after one use.

Compared to the use of conventional volume controllers such as syringes and pumps, a thermally-controlled sample delivery system of the invention has fewer moving parts which may wear out or require extensive maintenance. Moreover, since the sample delivery system may be independent of an analytical instrument, other benefits are realized. For example, the sample delivery channels can be made of low cost materials such as plastic capillary tubing since optical quality or integrated electrodes are not required. Accordingly, single use of a channel is attractive which can eliminate a cleaning step and/or cross-contamination.

In addition, since the channels typically are not used directly in an analytical technique, the channels may be readily moveable and have a higher degree of tolerance for positioning. That is, since the detection system of the analytical device typically remains stationary, the optical alignment of a liquid detection capillary needs to be done once for optimal accuracy during the analysis of a plurality of samples. Furthermore, if the sample delivery system contains a chemical reagent and is used to perform a reaction, any particulates present or formed during the reaction easily can be filtered prior to introduction of the reaction products to an analytical device thereby preventing clogging and/or inaccurate analysis. These above features permit simple and inexpensive automation robotics to be used.

Compared to using capillary action to deliver, mix and/or react chemicals, a sample delivery system of the invention which uses pressure exhibits several advantages. The surface of a channel of a sample delivery system of the invention may be hydrophilic or hydrophobic in contrast to a capillary action surface which requires a hydrophilic surface. Also with respect to the surface of the channel, the reproducibility of sample solution metering is independent of the surface characteristics and sample constituents. In addition, the sample delivery system of the invention allows direct control over the metering of samples and reagents, and permits bubble segregation to be practiced routinely.

Compared to electro-osmotic flow for delivering, mixing and/or reacting chemicals, a sample delivery system of the invention which uses pressure exhibits some of the same advantages compared to using capillary action discussed above, i.e., surface characteristics and reproducibility of solution metering. Moreover, the sample delivery system of the invention typically is unrestricted in its solution composition for conducting analysis and/or chemical reactions. That is, variables such as pH, ionic strength, buffer composition, chemical additives and solvents often are unlimited depending upon the particular application. These variables typically are restricted for effective electro-osmotic flow to occur.

Therefore, as described above, the present invention allows for high speed delivery of samples for the performance of microscale reactions and/or analysis of biological samples without the complexity, time, labor and biohazard exposure of conventional techniques. Additional aspects and embodiments of the invention are apparent upon consideration of the foregoing disclosure. Accordingly, the scope of the invention is limited only by the scope of the appended claims.

The invention may be embodied in other specific forms.
What is claimed is:

1. A thermally-controlled sample delivery system comprising:
    a housing defining a channel, the channel comprising an open end and a closed end;
    an insulator partition within the channel, an exterior insulator in thermal communication with the channel, or a combination of both;
    a thermally expandable fluid disposed within the channel; and
    a volume controller, which is a temperature control device, in thermal communication with the closed end of the channel to regulate the volume of the thermally expandable fluid disposed within the channel,
    wherein the volume controller is used to transport a sample in the channel.

2. A thermally-controlled sample delivery system comprising:
    a housing defining a channel, the channel comprising an open end and a closed end;
    at least one chemical reagent that is capable of interacting with a sample or a component of a sample disposed within the channel;
    an insulator partition within the channel, an exterior insulator in thermal communication with the channel, or a combination of both;
    a thermally expandable fluid disposed within the channel; and
    a volume controller, which is a temperature control device, in thermal communication with the closed end of the channel to regulate the volume of the thermally expandable fluid disposed within the channel,
    wherein the volume controller is used to transport a sample in the channel.

3. The thermally-controlled sample delivery system of claim 2 wherein the chemical reagent is immobilized within the channel.

4. The thermally-controlled sample delivery system of claim 2 wherein the chemical reagent is selected from the group consisting of an oligonucleotide, a peptide nucleic acid, a binding protein, an enzyme, a substrate, a ligand, a receptor, an antibody and an antigen.

5. The thermally-controlled sample delivery system of claim 2 further comprising a stabilizer for the chemical reagent.

6. The thermally-controlled sample delivery system of claim 2 wherein the chemical reagent is labeled with a detectable moiety or a chemical modifying moiety.

7. The thermally-controlled sample delivery system of claim 2 wherein the chemical reagent comprises a first set of chemical reagents and a second set of chemical reagents, and
    the first set of chemical reagents is spaced apart from the second set of chemical reagents.

8. A thermally-controlled sample delivery system comprising:
    a housing defining a channel, the channel comprising an open end and a closed end;
    an insulator partition within the channel, an exterior insulator in thermal communication with the channel, or a combination of both;
    a thermally expandable fluid disposed within the channel; and
    a volume controller, which is a temperature control device, in thermal communication with the closed end of the channel to regulate the volume of the thermally expandable fluid disposed within the channel,
    wherein the volume controller is used to transport a sample in the channel and the channel is a polymeric tubing material or etched or molded into the surface of a substrate.

9. A thermally-controlled sample delivery system comprising:
    a housing defining a channel, the channel comprising an open end and a closed end;
    an insulator partition within the channel, an exterior insulator in thermal communication with the channel, or a combination of both;
    a thermally expandable fluid disposed within the channel; and
    a volume controller, which is a temperature control device, in thermal communication with the closed end of the channel to regulate the volume of the thermally expandable fluid disposed within the channel,
    wherein the volume controller is used to transport a sample in the channel, and the channel is formed by enclosing a longitudinally open channel which has been etched or molded into an organic or an inorganic substrate defining said housing.

10. A thermally-controlled sample delivery system comprising:
    a housing defining a channel, the channel comprising an open end and a closed end;

a thermally expandable fluid disposed within the channel;
a volume controller, which is a temperature control device, in thermal communication with the closed end of the channel to regulate the volume of the thermally expandable fluid disposed within the channel; and
a second temperature control device defining a first conduit and a second conduit, where the temperature of each of the conduits is regulated independently, wherein the volume controller is used to transport a sample in the channel and the second temperature control device moves in a direction parallel to the length of the channel.

11. A scientific instrument comprising:
a thermally-controlled sample delivery system comprising:
   a housing defining a channel, the channel comprising an open end and a closed end,
   an insulator partition within the channel, an exterior insulator in thermal communication with the channel, or a combination of both;
   a thermally expandable fluid disposed within the channel, and
   a volume controller, which is a temperature control device, in thermal communication with the closed end of the channel to regulate the volume of the thermally
   expandable fluid disposed within the channel, wherein the volume controller is used to transport a sample in the channel; and
   a device in fluid communication with the thermally-controlled sample delivery system, wherein the device is selected from the group consisting of a blood testing device, an immunoassay device, a calorimetric device, an assay device, a toxin detection device, a chemical synthesis device, a sequencing device, a peptide or nucleotide sequencing device, a peptide or nucleotide amplification device, a peptide or nucleotide modification device, an enzyme screening device, a receptor-ligand reaction screening device, and combinations thereof.

12. The scientific instrument of claim 11 further comprising a computer in communication with the temperature control device to control the temperature control device.

13. A method for delivering a sample into a channel comprising the steps of:
   (a) providing a thermally-controlled delivery system comprising:
      (i) a housing defining a channel, the channel comprising an open end and a closed end;
      (ii) an insulator partition within the channel, an exterior insulator in thermal communication with the channel, or a combination of both; and
      (iii) a temperature control device in thermal communication with the closed end of the channel;
   (b) exposing the open end of the channel to a sample; and
   (c) contracting a thermally expandable fluid disposed within the channel using the temperature control device to transport at least a portion of the sample into the channel.

14. The method of claim 13 wherein introducing the sample into the channel is effected by non-thermally regulated means.

15. The method of claim 13 further comprising the step of expanding the thermally expandable fluid.

16. The method of claim 13 further comprising the step of expanding the thermally expandable fluid subsequent to step (c) to expel a portion of the sample.

17. The method of claim 13 wherein the channel comprises a capillary.

18. The method of claim 13 wherein the thermally expandable fluid comprises a gas.

19. The method of claim 13 further comprising the step of providing a second temperature control device in thermal communication with the channel for independently regulating a temperature.

20. The method of claim 13 further comprising the step of analyzing for a component in the sample.

21. A method for delivering a sample into a channel comprising the steps of:
   (a) providing a thermally-controlled delivery system comprising:
      (i) a housing defining a channel, the channel comprising an open end and a closed end; and
      (ii) a temperature control device in thermal communication with the closed end of the channel;
   (b) exposing the open end of the channel to a sample;
   (c) contracting a thermally expandable fluid disposed within the channel using the temperature control device to transport at least a portion of the sample into the channel;
   (d) expanding the thermally expandable fluid to expel the portion of the sample into a sample plug formation device, wherein the sample plug formation device comprises:
      a housing defining
         a separation channel comprising a longitudinal axis, and
         an introduction channel which forms a juncture with the separation
      channel;
   (e) applying a first pressure differential to the introduction channel to transport a portion of the sample in communication with the introduction channel to the juncture; and
   (f) applying a second pressure differential to the separation channel to transport another portion of the sample in the juncture into the separation channel to form a sample plug.

22. A method for delivering samples into a channel separated by a gas, the method comprising the steps of:
   (a) providing a thermally-controlled delivery system comprising:
      (i) a housing defining a channel the channel comprising an open end and a closed end; and
      (ii) a temperature control device in thermal communication with the closed end of the channel;
   (b) exposing the open end of the channel to a first sample;
   (c) contracting a thermally expandable fluid disposed within the channel using the temperature control device to transport at least a portion of the first sample into the channel;
   (d) exposing the open end of the channel to a gas;
   (e) contracting a thermally expandable fluid disposed within the channel using the temperature control device to transport a volume of the gas into the channel;
   (f) exposing the open end of the channel to a second sample;
   (g) contracting a thermally expandable fluid disposed within the channel using the temperature control device to transport at least a portion of the second sample into the channel.

23. The method of claim 22 wherein the second sample is the first sample.

* * * * *